United States Patent [19]

Blumbergs et al.

[11] 4,111,651
[45] Sep. 5, 1978

[54] SULFONIC ANHYDRIDES IN PEROXYGEN BLEACHING

[75] Inventors: John H. Blumbergs, Highland Park; Joseph H. Finley, Metuchen; Burton M. Baum, Princeton, all of N.J.

[73] Assignee: FMC Corporation, Philadelphia, Pa.

[21] Appl. No.: 838,851

[22] Filed: Oct. 3, 1977

[51] Int. Cl.$^2$ .............................. D06I 3/02; D06I 3/04
[52] U.S. Cl. ........................................ 8/111; 252/95; 252/99; 252/186
[58] Field of Search ................. 8/111.5, 111; 252/186, 252/95, 99

[56] References Cited

U.S. PATENT DOCUMENTS

| | | | |
|---|---|---|---|
| 2,284,477 | 5/1942 | Reichert | 260/502 |
| 2,955,905 | 10/1960 | Davies et al. | 8/111 |
| 3,211,773 | 10/1965 | Lederer | 252/186 |
| 3,298,775 | 1/1967 | Malafosse | 8/101 |
| 3,321,497 | 5/1967 | Matzner | 260/397.7 |
| 3,532,634 | 10/1970 | Woods | 252/95 |
| 3,775,333 | 11/1973 | Loffelman | 252/99 |
| 3,886,078 | 5/1975 | Loffelman | 252/102 |
| 3,912,648 | 10/1975 | Brady et al. | 252/102 |
| 3,919,102 | 11/1975 | Kuhling | 252/99 |

FOREIGN PATENT DOCUMENTS

90,980 11/1973 Japan.
1,802,015 10/1968 United Kingdom.

*Primary Examiner*—Donald Levy
*Attorney, Agent, or Firm*—Robert D. Jackson; Frank Ianno

[57] ABSTRACT

A process of removing soil and/or stains from fabrics by immersing the fabrics in a peroxygen bleach bath containing as a peroxygen activator a sulfonic anhydride of the formula:

$$R_1SO_2OSO_2R_2$$

wherein each of $R_1$ and $R_2$ is selected from the class consisting of an alkyl radical of 1 to 18 carbon atoms; a cycloalkyl radical of 3 to 7 carbon atoms; a phenyl radical; a naphthyl radical and a heterocyclic radical having 1 ring or 2 fused rings, said ring or rings containing 5 to 6 members of which 1 to 2 are heteroatoms selected from the group consisting of nitrogen, oxygen and sulfur, it being understood that $R_1$ and $R_2$ can be identical or different except where they are phenyl or naphthyl in which case $R_1$ and $R_2$ are always different. Also described are dry blend compositions containing the bleach bath components.

7 Claims, No Drawings

SULFONIC ANHYDRIDES IN PEROXYGEN BLEACHING

This invention relates to active oxygen compositions. In particular, the invention is concerned with activated peroxygen compounds and their application to laundering operations.

The use of bleaching agents as laundering aids is well known. In fact, such entities are considered necessary adjuncts for cleaning today's fabrics which embrace a wide spectrum of synthetic, natural and modified natural fiber systems, each differing in washing characteristics.

Laundry bleaches generally fall into one of two categories; active oxygen-releasing or peroxygen and active chlorine-releasing. Of the two, the chlorine bleach is more likely to react with the various components of a detergent washing formulation than peroxygen bleaches. Moreover, fabrics treated with chlorine bleaches exhibit significant loss of strength and depending on the frequency of bleaching, the useful life of the cloth may be appreciably reduced; with dyed fabrics, colors are often degraded. Another objection to chlorine bleaches is their pronounced tendency to cause yellowing, particularly with synthetics and resin treated fabrics. Peroxygen bleaches are substantially free of such adverse side effects.

Despite their many advantages, bleaching agents of the active oxygen-releasing type are as a class not optimally effective until use temperatures exceed about 85° C., usually 90° C., or higher. This rather critical temperature-dependency of peroxygen bleaching agents and especially the persalt bleaches such as sodium perborate poses a rather serious drawback since many household washing machines are now being operated at water temperatures less than about 60° C., well below those necessary to render bleaching agents such as the perborates adequately effective. Although the near boiling washing temperatures employed in Europe and some other countries favor the use of peroxygen bleaches, it can be expected that such temperatures will be lowered in the interest of conserving energy. Consequently, where a comparatively high order of bleaching activity at reduced temperature is desired, resort must be had to chlorine bleaches despite their attendant disadvantages, i.e., impairment of fabric strength, fabric discoloration, etc.

In an effort to realize the full potential of peroxygen bleaches, such materials have been the focus of considerable research and development effort over the years. One result of these investigations was the finding that certain substances, activators as they are usually called, have the capacity of amplifying the bleaching power of peroxygen compounds below about 60° C. where many home washing machines are commonly operated, or preferably operated. Although the precise mechanism of peroxygen bleach activation is not known, it is believed that activator-peroxygen interaction leads to the formation of an intermediate species which constitutes the active bleaching entity. In a sense, then, the activator-peroxygen component functions as a precursor system by which the in situ generation of species providing effective bleaching means is made possible.

Although numerous compounds have been proposed and tested as peroxygen bleach activators, a satisfactory candidate has thus far not been forthcoming. Perhaps the primary objection is the failure to provide the desired degree of bleaching activity within the limitations imposed by economically feasible practice. Thus, it is often necessary to utilize the activator compound in inordinately high concentrations in order to achieve satisfactory results; in other instances, it is found that a given activator is not generally applicable and thus may be used advantageously only in conjunction with rather specific and delimited types of peroxygen bleaching agents. Other disadvantages characterizing many of the activator compounds thus far contemplated include, for example, the difficulties associated with their incorporation into detergent powder compositions including stability problems and short shelf life. Since many of the activators are liquids under normal conditions, the blending of such materials into solid products is not practical, at least so far as home application is concerned. Moreover, ancillary techniques specifically devised for purposes of facilitating activator-detergent powder blending in such instances are often economically prohibitive, the results obtained failing to justify the involved costs.

Classes of compounds which are representative of prior art activators for peroxygen bleaches include carboxylic acid anhydrides disclosed in U.S. Pat. Nos. 2,284,477, 3,532,634 and 3,298,775; carboxylic esters disclosed in U.S. Pat. No. 2,955,905; N-substituted, N-acylnitrobenzenesulfonamides disclosed in U.S. Pat. No. 3,321,497; N-benzoylsaccharin disclosed in U.S. Pat. No. 3,886,078; N-acyl compounds such as those described in U.S. Pat. Nos. 3,912,648 and 3,919,102 and aromatic sulfonyl chlorides disclosed in Japanese Patent Publication No. 90980 of Nov. 27, 1973.

While certain of these activators are effective in varying degrees, there is a continuing need for candidate compounds of improved performance and properties.

It has now been discovered that the bleaching capacity of peroxygen bleaches at low temperatures is increased by contacting them with a sulfonic anhydride activator compound and the provision of bleaching compositions containing such components and the use thereof alone or in conjunction with conventional laundering processes and materials to treat soiled and/or stained fabrics constitutes the principal object and purpose of the invention. Other objects and purposes will become apparent subsequently herein.

The sulfonic anhydride activator compounds aforesaid can be depicted by the following formula:

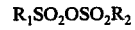

$$R_1SO_2OSO_2R_2$$

wherein each of $R_1$ and $R_2$ is selected from the class consisting of an alkyl radical of 1 to 18 carbon atoms; a cycloalkyl radical of 3 to 7 carbon atoms; a phenyl radical; a naphthyl radical and a heterocyclic radical having 1 ring or 2 fused rings, said ring or rings containing 5 to 6 members of which 1 to 2 are heteroatoms selected from the group consisting of nitrogen, oxygen and sulfur, it being understood that $R_1$ and $R_2$ can be identical or different except where they are phenyl or naphthyl in which case $R_1$ and $R_2$ are always different.

Another proviso attached to the characterization of the herein activators is that they exhibit sufficient solubility in the bleaching system in order to provide the requisite degree of activation for the active oxygen-releasing bleaching agent.

The sulfonic anhydrides of the invention belong to a known class, the description of which is set forth in the technical literature. Although they can be synthesized in a number of ways, for purposes herein they are conveniently prepared by reacting the requisite sulfonyl chloride and silver sulfonate in accordance with the following equation:

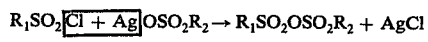

$R_1SO_2Cl + AgOSO_2R_2 \rightarrow R_1SO_2OSO_2R_2 + AgCl$

In carrying out the preparation, the acid chloride and silver salt are placed in a solvent and the mixture allowed to react. Stirring or other agitation means is employed to aid dissolution and maintain the reaction in a homogeneous state. Reaction temperatures are desirably restricted to about room temperature although temperatures up to about 100° C. can be employed. After the reaction is complete, the silver chloride is removed using any of the typical separation techniques, e.g., filtration, centrifugation or the like. The filtrate is evaporated leaving a solid residue of the sulfonic anhydride which is normally of sufficient purity whereby it can be used directly in peroxygen bleaching.

Examples of solvents for carrying out the reaction include any of the usually liquid, relatively inert organic liquids and in this connection the aliphatic chlorinated hydrocarbons are especially suitable, the chlorinated lower alkanes such as dichloromethane being preferred. For further details and information on the preparation of the sulfonic anhydrides as above described, reference is made to J. Prakt. Chem. [27], 128, 65 (1930) the disclosure of which is incorporated herein.

The condensation of a sulfonyl chloride with a silver sulfonate to produce sulfonic anhydrides is an organic synthesis reaction of remarkable scope and general applicability. In fact, it appears to be limited only with respect to the availability of reactants. There are, however, disclosed in the chemical journals, the description and preparation of a veritable host of organic sulfonyl chlorides and organic sulfonates and since their functions are readily interconvertible, the disclosure of one reactant is in effect a disclosure of the other. Accordingly, a great many anhydrides can be prepared falling within the scope of the formula wherein $R_1$ and $R_2$ can be varied extensively not only as regards the basic hydrocarbon and heterocyclic radicals but also as regards substituents attached thereto such as for instance chlorine, bromine, fluorine, alkoxyl, alkyl, nitro, cyano, carboxamido, hydroxyl, sulfo, or any substituent which does not interfere with the novel and basic characteristics of the sulfonic anhydride as an activator for peroxygen. Where there are $C_{12}$–$C_{18}$ alkyl groups present, the resulting sulfonic anhydride will not only function as a peroxygen activator but also exhibit detergent properties owing to the presence of the surface active higher alkyl radicals. Examples of sulfonic anhydrides herein which can be synthesized by the aforedescribed reaction from known sulfonyl chlorides and/or silver salts of sulfonic acids are listed below.

Symmetrical Alkyl Sulfonic Anhydrides $(CH_3SO_2)_2O$
$Iso\text{-}C_3H_7SO_2)_2O$
$(n\text{-}C_4H_9SO_2)_2O$
$(CF_3SO_2)_2O$
$(C_6H_{13}SO_2)_2O$
$(C_7H_{15}SO_2)_2O$
$(C_{10}H_{21}SO_2)_2O$
$(C_9H_{19}CHNO_2SO_2)_2O$
$(C_{12}H_{25}SO_2)_2O$
$(C_{16}H_{33}SO_2)_2O$
$(C_2H_5CHClCH_2SO_2)_2O$
$(C_3H_7CBrNO_2SO_2)_2O$
$(CHCl_2CH_2CHClCH_2SO_2)_2O$
$(C_4F_9SO_2)_2O$
$(C_2H_5CHOHCH_2SO_2)_2O$
$(C_2H_5CF_2CF_2SO_2)_2O$
$(CF_3CBrFSO_2)_2O$
$(CH_3CHClSO_2)_2O$
$(CH_2MeOCH_2SO_2)_2O$
$(CF_3CHFSO_2)_2O$
$(CH_2PhCH_2SO_2)_2O$
$(C_8F_{17}SO_2)_2O$

Unsymmetrical Alkyl Sulfonic Anhydrides $CH_3SO_2OSO_2C_3H_7$
$C_4H_9CHClCH_2SO_2OSO_2C_2H_5$
$CHCl_2CH_2CHClCH_2CHClCH_2SO_2OSO_2C_3H_7$
$C_5H_{11}CBrNO_2SO_2OSO_2C_4H_{9\text{-}n}$
$CF_3SO_2OC_5H_{11}$
$C_{10}H_{21}SO_2OSO_2C_7H_{15}$
$C_2H_5SO_2OSO_2CBrFCF_3$
$nC_4H_9SO_2OSO_2CHFCF_3$
$CH_2BrSO_2OSO_2C_2H_5$
$CF_3SO_2OSO_2C_{10}H_{21}$
$C_7H_5SO_2OSO_2CH_2Br$
$C_8F_{17}SO_2OSO_2CH_3$
$C_8F_{17}SO_2OSO_2C_2H_5$
$C_5H_{11}COCH_2CH_2SO_2OSO_2CH_3$
$C_2H_5CHOHCH_2SO_2OSO_2C_3H_7$
$C_2H_5CF_2CF_2SO_2OSO_2C_4H_9$

Cycloalkane Sulfonic Anhydrides $(C_3H_5SO_2)_2O$
$(C_5H_9SO_2)_2O$
$(C_6H_{11}SO_2)_2O$
$C_5H_9SO_2OSO_2C_6H_{11}$
$(4\text{-}MeC_6H_{10}SO_2)_2O$
$4\text{-}MeC_6H_{10}SO_2OSO_2C_5H_{11}$
$(2\text{-}ClC_6H_{10}SO_2)_2O$
$(C_7H_{13}SO_2)_2O$
$C_7H_{13}SO_2OSO_2C_6H_{11}$
$C_6H_{11}SO_2OSO_2C_3H_5$
$1\text{-}OHC_7H_{12}SO_2OSO_2C_6H_{11}$

Unsymmetrical Aryl And Other Sulfonic Anhydrides $CH_3SO_2OSO_2C_6H_5$
$C_2H_5SO_2OSO_2C_6H_4\text{-}p\text{-}C_2H_5O$
$n\text{-}C_3H_7SO_2OSO_2C_6H_4\text{-}p\text{-}CF_3$
$m\text{-}Cl\text{-}C_6H_4SO_2OSO_2C_6H_4\text{-}p\text{-}CH_3O$
$C_{12}H_{25}\text{-}C_6H_4SO_2OSO_2C_6H_5$
$2,4\text{-}Cl_2\text{-}C_6H_3SO_2OSO_2C_6H_4\text{-}p\text{-}CH_3$

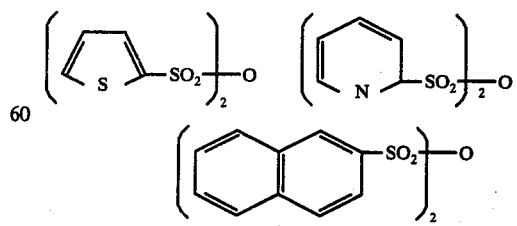

-continued

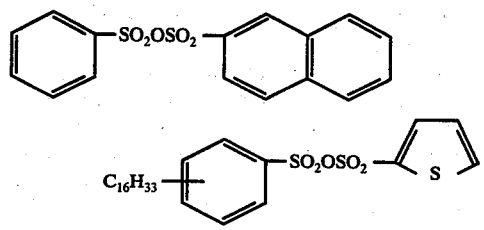

Sulfonic anhydrides of the invention which have given excellent results as a peroxygen activator are those members of the formula wherein $R_1$ is lower alkyl and fluorinated lower alkyl and wherein $R_2$ is lower alkyl, fluorinated lower alkyl, phenyl, lower alkylated phenyl and chlorinated phenyl. By lower alkyl is meant an alkyl radical of from 1 to about 4 carbon atoms.

In accordance with the invention, low temperature bleaching (i.e. below about 60° C) of stained and/or soiled fabrics is effected by contacting them with a solution containing a sulfonic anhydride activator herein and an active oxygen-releasing compound. The active oxygen-releasing compounds include such peroxygen compounds as hydrogen peroxide or those peroxygen compounds that liberate hydrogen peroxide in aqueous media. Examples of such peroxygen compounds are urea peroxide, alkali metal perborates, percarbonates, perphosphates, persulfates, monopersulfates and the like. Combinations of two or more peroxygen bleaches can be used where desired. The same holds true in the case of the activators. Although any number of peroxygen compounds are suitable in carrying out the invention, a preferred compound is sodium perborate tetrahydrate, since it is a readily available commercial product. Another suitable persalt is sodium carbonate peroxide.

Sufficient peroxygen compounds to provide from about 2 ppm to 2,000 ppm active oxygen in solution are used. For home bleaching applications, the concentration of active oxygen in the wash water is desirably from about 5 to 100 ppm, preferably about 15 to 60 ppm. Sodium perborate tetrahydrate, the preferred peroxygen compound, contains 10.4% active oxygen. The actual concentration employed in a given bleaching solution can be varied widely, depending on the intended use of the solution.

The concentration of the sulfonic anhydrides in the bleaching solution depends to a large extent on the concentration of the peroxygen compound which, in turn, depends on the particular use for which a given composition is formulated. Higher or lower levels can be selected according to the needs of the formulator. Overall, increased bleaching results are realized when the active oxygen of the peroxygen compound and sulfonic anhydride are present in a mole ratio in the range of from about 20:1 to 1:3, preferably from about 10:1 to 1:1.

Activation of the peroxygen bleaches is generally carried out in aqueous solution at a pH of from about 6 to about 12, most preferably 8.0 to 10.5. Since an aqueous solution of persalts or peracids is generally acidic, it is necessary to maintain the requisite pH conditions by means of buffering agents. Buffering agents suitable for use herein include any non-interfering compound which can alter and/or maintain the solution pH within the desired range, and the selection of such buffers can be made by referring to a standard text.

For instance, phosphates, carbonates, or bicarbonates, which buffer within the pH range of 6 to 12 are useful. Examples of suitable buffering agents include sodium bicarbonate, sodium carbonate, sodium silicate, disodium hydrogen phosphate, sodium dihydrogen phosphate. The bleach solution may also contain a detergent agent where bleaching and laundering of the fabric is carried out simultaneously. The strength of the detergent agent is commonly about 0.05% to 0.80% (wt.) in the wash water.

Although the activator, buffer and peroxygen compound can be employed individually in formulating the bleach solutions of the invention, it is generally more convenient to prepare a dry blend of these components and the resulting composition added to water to produce the bleach solution. A soap or organic detergent can be incorporated into the composition to give a solution having both washing and bleaching properties. Organic detergents suitable for use in accordance with the present invention encompass a relatively wide range of materials and may be of the anionic, non-ionic, cationic or amphoteric types.

The anionic surface active agents include those surface active or detergent compounds which contain an organic hydrophobic group and an anionic solubilizing group. Typical examples of anionic solubilizing groups are sulfonate, sulfate, carboxylate, phosphonate and phosphate. Examples of suitable anionic detergents which fall within the scope of the invention include the soaps, such as the water-soluble salts of higher fatty acids or rosin acids, such as may be derived from fats, oils, and waxes of animal, vegetable or marine origin, e.g., the sodium soaps of tallow, grease, coconut oil, tall oil and mixtures thereof; and the sulfated and sulfonated synthetic detergents, particularly those having about 8 to 26, and preferably about 12 to 22, carbon atoms to the molecule.

As examples of suitable synthetic anionic detergents the higher alkyl mononuclear aromatic sulfonates are preferred particularly the LAS type such as the higher alkyl benzene sulfonates containing from 10 to 16 carbon atoms in the alkyl group, e.g., the sodium salts such as decyl, undecyl, dodecyl (lauryl), tridecyl, tetradecyl, pentadecyl, or hexadecyl benzene sulfonate and the higher alkyl toluene, xylene and phenol sulfonates; alkyl naphthalene sulfonate, ammonium diamyl naphthalene sulfonate, and sodium dinonyl naphthalene sulfonate.

Other anionic detergents are the olefin sulfonates including long chain alkene sulfonates, long chain hydroxyalkane sulfonates or mixtures of alkenesulfonates and hydroxyalkanesulfonates. These olefin sulfonate detergents may be prepared, in known manner, by the reaction of $SO_3$ with long chain olefins (of 8–25 preferably 12–21 carbon atoms) of the formula $RCH = CHR_1$, where R is alkyl and $R_1$ is alkyl or hydrogen, to produce a mixture of sultones and alkenesulfonic acids, which mixture is then treated to convert the sultones to sulfonates. Examples of other sulfate or sulfonate detergents are paraffin sulfonates, such as the reaction products of alpha olefins and bisulfites (e.g. sodium bisulfite), e.g., primary paraffin sulfonates of about 10–20 preferably about 15–20 carbon atoms; sulfates of higher alcohols; salts of α-sulfofatty esters (e.g. of about 10 to 20 carbon atoms, such as methyl α-sulfomyristate or α-sulfotallowate).

Examples of sulfates of higher alcohols are sodium lauryl sulfate, sodium tallow alcohol sulfate; Turkey Red Oil or other sulfated oils, or sulfates of mono- or diglycerides of fatty acids (e.g. stearic monoglyceride monosulfate), alkyl poly(ethenoxy) ether sulfates such as the sulfates of the condensation products of ethylene oxide and lauryl alcohol (usually having 1 to 5 ethenoxy groups per molecule); lauryl or other higher alkyl glyceryl ether sulfonates; aromatic poly(ethenoxy) ether sulfates such as the sulfates of the condensation products of ethylene oxide and nonyl phenol (usually having 1 to 20 oxyethylene groups per molecule, preferably 2–12).

The suitable anionic detergents include also the acyl sarcosinates (e.g. sodium lauroylsarcosinate) the acyl ester (e.g. oleic acid ester) of isethionates, and the acyl N-methyl taurides (e.g. potassium N-methyl lauroyl or oleyl tauride).

Other highly preferred water soluble anionic detergent compounds are the ammonium and substituted ammonium (such as mono-, di- and triethanolamine), alkali metal (such as sodium and potassium) and alkaline earth metal (such as calcium and magnesium) salts of the higher alkyl sulfates, and the higher fatty acid monoglyceride sulfates. The particular salt will be suitably selected depending upon the particular formulation and the proportions therein.

Nonionic surface active agents include those surface active or detergent compunds which contain an organic hydrophobic group and a hydrophilic group which is a reaction product of a solubilizing group such as carboxylate, hydroxyl, amido or amino with ethylene oxide or with the polyhydration product thereof, polyethylene glycol.

As examples of nonionic surface active agents which may be used there may be noted the condensation products of alkyl phenols with ethylene oxide, e.g., the reaction product of octyl phenol with about 6 to 30 ethylene oxide units; condensation products of alkyl thiophenols with 10 to 15 ethylene oxide units; condensation products of higher fatty alcohols such as tridecyl alcohol with ethylene oxide; ethylene oxide addends of monoesters of hexahydric alcohols and inner ethers thereof such as sorbitol monolaurate, sorbitol mono-oleate and mannitol monopalmitate, and the condensation products of polypropylene glycol with ethylene oxide.

Cationic surface active agents may also be employed. Such agents are those surface active detergent compounds which contain an organic hydrophobic group and a cationic solubilizing group. Typical cationic solubilizing groups are amine and quaternary groups.

As examples of suitable synthetic cationic detergents there may be noted the diamines such as those of the type $RNHC_2H_4NH_2$ wherein R is an alkyl group of about 12 to 22 carbon atoms, such as N-2-aminoethyl stearyl amine and N-2-aminoethyl myristyl amine; amide-linked amines such as those of the type $R_1CONHC_2H_4NH_2$ wherein R is an alkyl group of about 9 to 20 carbon atoms, such as N-2 amino ethyl stearyl amide and N-amino ethyl myristyl amide; quaternary ammonium compounds wherein typically one of the groups linked to the nitrogen atom are alkyl groups which contain 1 to 3 carbon atoms, including such 1 to 3 carbon alkyl groups bearing inert substituents, such as phenyl groups, and there is present an anion such as halide, acetate, methosulfate, etc. Typical quaternary ammonium detergents are ethyl-dimethyl-stearyl ammonium chloride, benzyl-dimethyl-stearyl ammonium chloride, benzyl-diethyl-stearyl ammonium chloride, trimethyl stearyl ammonium chloride, trimethyl-cetyl ammonium bromide, dimethylethyl dilauryl ammonium chloride, dimethyl-propyl-myristyl ammonium chloride, and the corresponding methosulfates and acetates.

Examples of suitable amphoteric detergents are those containing both an anionic and a cationic group and a hydrophobic organic group, which is advantageously a higher aliphatic radical, e.g., of 10–20 carbon atoms. Among these are the N-long chain alkyl aminocarboxylic acids e.g. of the formula

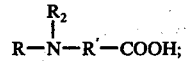

the N-long chain alkyl iminodicarboxylic acids (e.g. of the formula $RN(R'COOH)_2$) and the N-long chain alkyl betaines e.g. of the formula

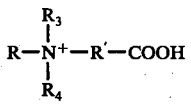

where R is a long chain alkyl group, e.g. of about 10–20 carbons, R' is a divalent radical joining the amino and carboxyl portions of an amino acid (e.g. an alkylene radical of 1–4 carbon atoms ), H is hydrogen or a salt-forming metal, $R_2$ is a hydrogen or another monovalent substituent (e.g. methyl or other lower alkyl), and $R_3$ and $R_4$ are monovalent substituents joined to the nitrogen by carbon-to-nitrogen bonds (e.g. methyl or other lower alkyl substituents). Examples of specific amphoteric detergents are N-alkyl-betaaminopropionic acid; N-alkyl-beta-iminodipropionic acid, and N-alkyl, N,N-dimethyl glycine; the alkyl group may be, for example, that derived from coco fatty alcohol, lauryl alcohol, myristyl alcohol (or a lauryl-myristyl mixture), hydrogenated tallow alcohol, cetyl, stearyl, or blends of such alcohols. The substituted aminopropionic and iminodipropionic acids are often supplied in the sodium or other salt forms, which may likewise be used in the practice of this invention. Examples of other amphoteric detergents are the fatty imidazolines such as those made by reacting a long chain fatty acid (e.g. of 10 to 20 carbon atoms) with diethylene triamine and monohalo-carboxylic acids having 2 to 6 carbon atoms, e.g. 1-coco-5-hydroxyethyl-5-carboxymethylimidazoline; betaines containing a sulfonic group instead of the carboxylic group; betaines in which the long chain substituent is joined to the carboxylic group without an intervening nitrogen atom, e.g. inner salts of 2-trimethylamino fatty acids such as 2-trimethylaminolauric acid, and compounds of any of the previously mentioned types but in which the nitrogen atom is replaced by phosphorus.

The instant compositions optionally contain a detergency builder of the type commonly added to detergent formulations. Useful builders herein include any of the conventional inorganic and organic water-soluble builder salts. Inorganic detergency builders useful herein include, for example, water-soluble salts of phosphates, pyrophosphates, orthophosphates, polyphosphates, silicates, carbonates, zeolites, including natural and synthetic and the like. Organic builders include various water-soluble phosphonates, polyphosphonates, polyhydroxysulfonates, polyacetates, carboxylates, polycarboxylates, succinates, and the like.

Specific examples of inorganic phosphate builders include sodium and potassium tripolyphosphates, phosphates, and hexametaphosphates. The organic polyphosphonates specifically include, for example, the sodium ad potassium salts of ethane 1-hydroxy-1,1-diphosphonic acid and the sodium and potassium salts of ethane-1,1,2-triphosphonic acid. Examples of these and other phosphorus builder compounds are disclosed in U.S. Pat. Nos. 3,159,581, 3,213,030, 3,422,021, 3,422,137, 3,400,176 and 3,400,148, incorporated herein by reference. Sodium tripolyphosphate is an especially preferred, water-soluble inorganic builder herein.

Non-phosphorus containing sequestrants can also be selected for use herein as detergency builders.

Specific examples of non-phosphorus, inorganic builder ingredients include water-soluble inorganic carbonate, bicarbonate, and silicate salts. The alkali metal, e.g. sodium and potassium, carbonates, bicarbonates, and silicates are particularly useful herein.

Water-soluble, organic builders are also useful herein. For example, the alkali metal, ammonium and substituted ammonium polyacetates, carboxylates, polycarboxylates and polyhydroxysulfonates are useful builders in the present compositions and processes. Specific examples of the polyacetate and polycarboxylate builder salts include sodium, potassium, lithium, ammonium and substituted ammonium salts of ethylenediaminetetraacetic acid, nitrilotriacetic acid, oxydisuccinic acid, mellitic acid, benzene polycarboxylic (i.e., penta- and tetra-) acids, carboxymethoxysuccinic acid and citric acid.

Highly preferred non-phosphorus builder materials (both organic and inorganic) herein include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Other preferred organic builders herein are the polycarboxylate builders set forth in U.S. Pat. No. 3,308,067, incorporated herein by reference. Examples of such materials include the water-soluble salts of homo- and copolymers of aliphatic carboxylic acids such as maleic acid, itaconic acid, mesaconic acid, fumaric acid, aconitic acid, citraconic acid and methylenemalonic acid.

The builders aforesaid, particularly the inorganic types, can function as buffers to provide the requisite alkalinity for the bleaching solution. Where the builder does not exhibit such buffer activity, an alkaline reacting salt can be incorporated in the formulation.

The dry blend compositions of the invention contain about 0.1 to 50% (wt.), preferably 0.5 to 20% (wt.) of the herein sulfonic anhydride activator. It will be appreciated that the concentration of activator will depend on the concentration of the peroxygen bleach compound which is governed by the particular degree of bleaching desired. Higher or lower levels within the range will be selected to meet the requirement of the formulator. As to the peroxygen bleaching agent, this is present to the extent of about 1 to 75% (wt.) of the composition, depending on the degree of bleaching activity desired. Generally speaking, optimal bleaching is obtained when the compositions are formulated with a peroxygen/sulfonic anhydride mole ratio in the range of from about 20:1 to 1:3, preferably about 10:1 to about 1:1. The composition will contain a buffering agent in sufficient quantity to maintain a pH of about 6 to 12 when the composition is dissolved in water. The buffering agent can constitute from about 1% to about 95% (wt.) of the dry blended composition.

The herein activated bleach compositions can be provided for use in combination with a detergent agent or as a fully-formulated built detergent. Such compositions will comprise from about 5 to 50% of the activated bleach system, from about 5 to 50% (wt.) of the detergent agent and optionally from about 1 to 60% (wt.) of a detergency builder which can also function as a buffer to provide the requisite pH range when the composition is added to water.

The compositions herein can include detergent adjunct materials and carriers commonly found in laundering and cleaning compositions. For example, various perfumes, optical brighteners, fillers, anti-caking agents, fabric softeners, and the like can be present to provide the usual benefits occasioned by the use of such materials in detergent compositions. Enzymes, especially the thermally stable proteolytic and lipolytic enzymes used in laundry detergents, also can be dry-mixed in the compositions herein.

The solid peroxygen bleaching compositions herein are prepared by simply admixing the ingredients. When preparing mixed detergent/bleaches, the peroxygen and activator can be mixed either directly with the detergent compound, builder, etc., or the peroxygen and activator can be separately or collectively coated with a water-soluble coating material to prevent premature activation of the bleaching agent. The coating process is conducted according to known procedures in the art utilizing known coating materials. Suitable coating materials include compounds such as magnesium sulfate hydrate, polyvinyl alcohol, or the like.

The following examples are illustrative of the compound of the invention:

EXAMPLE 1

1.76 g (0.01 mole) of benzenesulfonyl chloride and 2.03 g (0.01 mole) of silver methanesulfonate were combined in 15 ml of dichloromethane. The mixture was stirred for three days and filtered to remove silver chloride. The filtrate was evaporated to dryness, giving 1.45 g of a viscous liquid product.

EXAMPLE 2

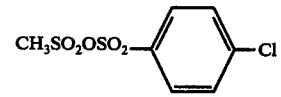

This sulfonic anhydride was prepared in the same manner as the previous example by combining 8.4 g (0.04 mole) of 4-chlorobenzenesulfonyl chloride and 8.12 g (0.04 mole) of silver methanesulfonate in 50 ml of dichloromethane. The solid product weighed 5.3 g; 49% yield.

EXAMPLE 3

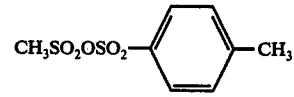

Following the procedure of the previous examples, this sulfonic anhydride was prepared by combining 7.62 g (0.04 mole) of p-toluenesulfonyl chloride with 8.12 g (0.04 mole) of silver methanesulfonate in 50 ml of dichloromethane. There was obtained 5.2 g (52% yield) of product.

EXAMPLE 4

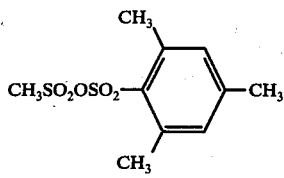

Following the procedure of the previous examples, this sulfonic anhydride was prepared by combining 4.4 g (0.02 mole) of mesitylenesulfonyl chloride (2,4,6-trimethylbenzenesulfonyl chloride) with 4.06 g (0.02 mole) of silver methanesulfonate in 25 ml of dichloromethane. After reacting overnight at room temperature, the mixture was filtered. Evaporation of the filtrate gave 3.99 g (72% yield) of product.

EXAMPLE 5

Cyclohexanesulfonic Anhydride

To a stirred solution of 35 ml of phosphorus trichloride in 300 ml of cyclohexane was bubbled (room temp) 167 ml/minute of sulfur dioxide and 83 ml/min of oxygen. After several hours, an additional 25 ml portion of phosphorus trichloride was added, followed by another portion. The solution was evaporated to a total volume of 100 ml in a rotary evaporator; on chilling, yielded 14.8 g of white crystals with mp 90°–93° C was deposited. Crystallization from cyclohexane gave 12.4 g of solid with mp 97°–100° C. (lit 106°–107° C.). The procedure of this Example was patterned after that disclosed in Ann. Vol. 572, pg. 79, (1952).

Anal: Calc'd for $C_{12}H_{22}S_2O_5$: C, 46.73; H, 6.54; S, 20.79. Found: C, 46.70; H, 7.24; S, 20.29.

This example illustrates another synthesis route for preparing sulfonic anhydrides. The procedure is practical only for symmetrical members.

Evaluation of Compounds as Bleach Activators

Compounds of the invention were evaluated for bleach activating efficacy by determining the increase in percent tea stain removal (%TSR) achieved by use of both the peroxygen source and activator compared with that obtained by use of the peroxygen source alone. Both tests were performed under otherwise identical low temperature laundering conditions. The increase in %TSR is called Δ%TSR. The evaluation was carried out in the presence of a detergent formulation and sodium perborate tetrahydrate as the source of peroxygen compound.

Tea-stained cotton and 65% dacron/35% cotton swatches (5 inches × 5 inches) used in these tests were prepared as follows: For each 50 swatches, 2000 ml of tap water was heated to boiling in a four-liter beaker. Reflectance readings were made on each swatch, using a Hunter Model D-40 Reflectometer before staining. Two family size tea bags were added to each beaker and boiling was continued for five minutes. The tea bags were then removed and 50 fabric swatches were added to each beaker. The dacron/cotton and 100% cotton swatches were boiled in the tea solution for seven and five minutes respectively, after which the entire content of each beaker was transferred to a centrifuge and rotated for about 0.5 minutes.

The swatches were then dried for thirty minutes in a standard household laundry drier. One hundred dry swatches were rinsed four times by agitating manually in 2000 ml portions of cold tap water. The swatches were dried in the household drier for approximately 40 minutes; they were allowed to age for at least three days before use. Reflectance readings for each swatch were taken prior to bleaching tests, using a Hunter Model D-40 Reflectometer.

Three stained cotton and polyester/cotton swatches were added to each of several stainless steel Terg-O-Tometer vessels containing 1000 ml of 0.15% detergent solution, maintained at a constant temperature of 105° F. The Terg-O-Tometer is a test washing device manufactured by the U.S. Testing Company. The detergent solution was prepared from a detergent formulation having the following composition (by weight):

25.0% — Sodium tripolyphosphate
7.5% — Sodium dodecylbenzenesulfonate (anionic surfactant)
4.0% — Alcohol ether sulfate (obtained from 1 mole of $C_{16}$–$C_{18}$ alcohol with 1 mole ethylene oxide (anionic surfactant)
6.5% — Alcohol ($C_{16}$–$C_{18}$) sulfate (anionic surfactant)
1.3% — Polyethylene glycol of about 6000 molecular wt.
35.4% — Sodium sulfate
11.0% — Sodium silicate
8.0% — Moisture
0.8% — Optical brightener
0.5% — Carboxymethylcellulose Measured quantities of sodium perborate tetrahydrate were added to each vessel to provide the desired quantity of active oxygen (A.O.) followed by an amount of activator compound to give the bleaching A.O. levels. In each test run, the activator was excluded from at least one Tert-O-Tometer vessel. The pH of each solution was adjusted to about 10.0 with 5% sodium hydroxide solution. The Terg-O-Tometer was operated at 100 cycles per minute for 15 or 30 minutes at the desired temperature. The swatches were then removed, rinsed under cold tap water and dried in a household clothing drier. Reflectance readings were taken on each swatch and percent tea stain removal (%TSR) was calculated as follows:

$$\%TSR = \frac{(\text{Reflectance After Bleaching}) - (\text{Reflectance Before Bleaching})}{(\text{Reflectance Before Staining}) - (\text{Reflectance Before Bleaching})} \times 100$$

The increase of %TSR, termed Δ%TSR, was calcuated by subtracting the average %TSR in runs where the perborate was present alone, from the average %TSR obtained in runs where both the activator and the perborate were present. The test results are given in Table I. As the Δ%TSR values clearly demonstrate, the activator compounds of the invention markedly improve the percentage of stain removal compared to the peroxygen bleach compound alone.

Pursuant to the requirements of the patent statutes, the principle of this invention has been explained and exemplified in a manner so that it can be readily practiced by those skilled in the art, such exemplification including what is considered to represent the best embodiment of the invention. However, it should be clearly understood within the scope of the appended claims, the invention may be practiced by those skilled

TABLE I

BLEACH TEST[1] RESULTS WITH SULFONIC ANHYDRIDES: $R_1SO_2OSO_2R_2$

| Compound | $R_1$ | $R_2$ | Active Oxygen A.$O_2$ ppm[2] | Mole Ratio of Peroxygen Compound/Activator | %TSR Cotton | %TSR Blend | Δ%TSR Cotton | Δ%TSR Blend |
|---|---|---|---|---|---|---|---|---|
| 1[3] | $CH_3$ | $CH_3$ | 60 | 1.4 | 65 | 40 | 44 | 25 |
| | " | " | 60 | 2 | 68 | 47 | 47 | 32 |
| | " | " | 60 | 2.4 | 52 | 25 | 31 | 12 |
| | " | " | 60 | 2.4 | 67 | 41 | 46 | 28 |
| | " | " | 60 | 3.5 | 66 | 38 | 45 | 25 |
| | " | " | 60 | 2 | 47 | 21 | 18 | 8 |
| 2 | $CH_3$ | $C_6H_5$ | 60 | 2 | 71 | 45 | 43 | 32 |
| | " | " | 60 | 2 | 70 | 55 | 41 | 42 |
| | " | " | 30 | 2.7 | 47 | 15 | 21 | 1 |
| 3 | $CH_3$ | p-$C_6H_4Cl$ | 60 | 0.86 | 75 | 69 | 51 | 59 |
| | " | " | 60 | 0.82 | 80 | 71 | 55 | 59 |
| | " | " | 15 | 1.9 | 46 | 23 | 17 | 9 |
| | " | " | 15 | 1.9 | 30 | 13 | 19 | 5 |
| 4 | $CH_3$ | p-$C_6H_4CH_3$— | 60 | 2 | 71 | 63 | 49 | 55 |
| | " | " | 60 | 2 | 73 | 60 | 50 | 50 |
| | " | " | 60 | 2 | 69 | 59 | 45 | 49 |
| | " | " | 60 | 2 | 73 | 61 | 48 | 49 |
| 5[4] | $CH_3$ | 2,4,6—$(CH_3)_3$—$C_6H_2$— | 60[4] | 2 | 67 | 55 | 38 | Purchased |
| | " | " | 60[4] | 2 | 61 | 51 | 34 | 39 |
| 6[5] | $CF_3$ | $CF_3$ | 60 | 2 | 32 | 10 | 9 | 4 |
| 7 | cyclo $C_6H_{11}$ | cyclo $C_6H_{11}$ | 60 | 2 | 60 | 29 | 37 | 20 |

[1]All tests performed at 100–105° F for thirty minutes.
[2]Sodium perborate tetrahydrate used as active oxygen source, unless otherwise specified.
[3]Purchased from Aldrich Chemical Co.
[4]Sodium carbonate peroxide as active oxygen source.
[5]Purchsed from Pfaltz & Bauer, Flushing, N.Y.

What is claimed is:

1. A process for the low temperature bleaching of stained and/or soiled fabrics which comprises treating them with an aqueous peroxygen bleaching solution having a pH of about 6 to about 12 and containing as a peroxygen activator therefor, an effective amount of a sulfonic anhydride having the formula:

$R_1SO_2OSO_2R_2$ wherein each of $R_1$ and $R_2$ is selected from the class consisting of an alkyl radical of 1 to 18 carbon atoms; a cycloalkyl radical of 3 to 7 carbon atoms; a phenyl radical; a naphthyl radical and a heterocyclic radical having 1 ring or 2 fused rings, said ring or rings containing 5 to 6 members of which 1 to 2 are heteroatoms selected from the group consisting of nitrogen, oxygen and sulfur, it being understood that $R_1$ and $R_2$ can be identical or different except where they are phenyl or naphthyl in which case $R_1$ and $R_2$ are always different.

2. The process according to claim 1 wherein the mole ratio of peroxygen to activator is from about 20:1 to about 1:3.

3. The process according to claim 2 wherein the peroxygen is sodium perborate tetrahydrate.

4. The process according to claim 2 wherein the quantity of peroxygen is sufficient to provide from about 2 ppm to about 2000 ppm of active oxygen.

5. The process according to claim 1 wherein the bleach solution contains a detergent agent.

6. The process according to claim 1 wherein the pH of the bleach solution is maintained by means of a buffering agent.

7. The process according to claim 1 wherein $R_1$ is selected from the class consisting of lower alkyl and fluorinated lower alkyl and $R_2$ is selected from the class consisting of alkyl, fluorinated lower alkyl, phenyl, lower alkylated phenyl and chlorinated phenyl.

* * * * *

UNITED STATES PATENT AND TRADEMARK OFFICE
CERTIFICATE OF CORRECTION

PATENT NO. : 4,111,651
DATED : September 5, 1978
INVENTOR(S) : John H. Blumbergs, et al It is certified that error appears in the above-identified patent and that said Letters Patent are hereby corrected as shown below:

Column 3, line 60, ""ISO-$C_3H_7SO_2)_2O$" should read --(ISO-$C_3H_7SO_2)_2O$--. Line 65, ""$C_{10}H_{21}SO_2)_2O$" should read --$(C_{10}H_{21}SO_2)_2O$--. Column 13, Table I, subheading "Active Oxygen A.$O_2$" should read --Active Oxygen A.O.--. Table 1, heading "Mole Ratio of Peroxygen Compound/Activator", figure "0.82" should read --0.86--. Column 14, Table I, under heading Δ %TSR Blend, "Purchased" should read --40--.

Signed and Sealed this

Seventeenth Day of April 1979

[SEAL]

Attest:

RUTH C. MASON
Attesting Officer

DONALD W. BANNER
Commissioner of Patents and Trademarks